United States Patent
Kang et al.

(10) Patent No.: US 7,626,186 B2
(45) Date of Patent: Dec. 1, 2009

(54) MOBILE ELECTRON BEAM RADIATION STERILIZING APPARATUS

(75) Inventors: Kejun Kang, Beijing (CN); Huayi Zhang, Beijing (CN); Zhiqiang Chen, Beijing (CN); Yuanjing Li, Beijing (CN); Chuanxiang Tang, Beijing (CN); Yaohong Liu, Beijing (CN); Huaibi Chen, Beijing (CN); Huaping Tang, Beijing (CN); Nan Jiang, Beijing (CN); Dongsheng Zhang, Beijing (CN); Yu He, Beijing (CN); Feng Gao, Beijing (CN); Weiqiang Guan, Beijing (CN); Jian Li, Beijing (CN); Yanfeng Cao, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 250 days.

(21) Appl. No.: 11/811,313

(22) Filed: Jun. 8, 2007

(65) Prior Publication Data

US 2008/0131312 A1 Jun. 5, 2008

(30) Foreign Application Priority Data

Jul. 17, 2006 (CN) .................. 2006 1 0098858
Sep. 21, 2006 (CN) .................. 2006 1 0127018

(51) Int. Cl.
*A61L 2/00* (2006.01)

(52) U.S. Cl. ................. 250/492.3; 250/435; 250/515.1; 250/492.1; 250/493.1; 250/505.1; 204/157.44; 378/57; 378/55; 422/186; 422/22

(58) Field of Classification Search .............. 250/492.3, 250/435, 492.1, 493.1, 505.1, 515.1; 204/157.44; 422/186, 22; 378/57, 55
See application file for complete search history.

(56) References Cited

U.S. PATENT DOCUMENTS

| | | | | |
|---|---|---|---|---|
| 5,554,856 A | * | 9/1996 | Bidnyy et al. | 250/455.11 |
| 5,557,109 A | * | 9/1996 | Bidnyy et al. | 250/455.11 |
| 5,744,811 A | * | 4/1998 | Schonberg et al. | 250/492.3 |
| 5,814,821 A | * | 9/1998 | Reusch et al. | 250/492.3 |
| 6,191,424 B1 | * | 2/2001 | Stirling et al. | 250/455.11 |
| 6,542,580 B1 | * | 4/2003 | Carver et al. | 378/57 |
| 7,459,706 B2 | * | 12/2008 | Fontcuberta et al. | 250/492.3 |
| 2005/0167613 A1 | * | 8/2005 | Bol et al. | 250/492.1 |

FOREIGN PATENT DOCUMENTS

RU 2074004 C1 * 2/1995

* cited by examiner

*Primary Examiner*—Robert Kim
*Assistant Examiner*—Michael J Logie
(74) *Attorney, Agent, or Firm*—Osha • Liang LLP

(57) ABSTRACT

A mobile electron beam radiation sterilizing apparatus includes a movable chassis vehicle; a cabinet body installed on the chassis vehicle; an electron accelerator, which generates electron beam for articles to be radiation-processed, wherein the electron accelerator is provided in the cabinet body; an accelerator control box, which controls operation of the electron accelerator, a radiation shielding system comprised of: a stationary shielding body covering the electron accelerator; a pair of rotatable shielding doors, through which a passage is formed for an article to be processed to enter or exit, rotatably connected to the stationary shielding body; a motor for switching on and switching off the rotatable shielding doors.

20 Claims, 7 Drawing Sheets

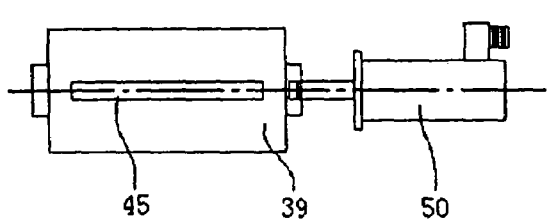
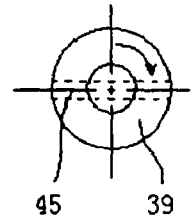
Fig.8A    Fig.8B
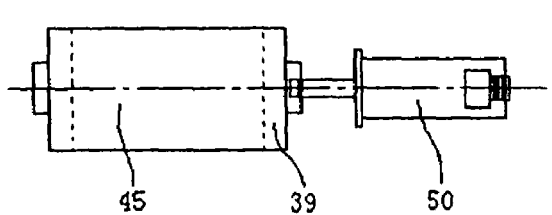
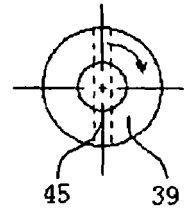
Fig.9A    Fig.9B
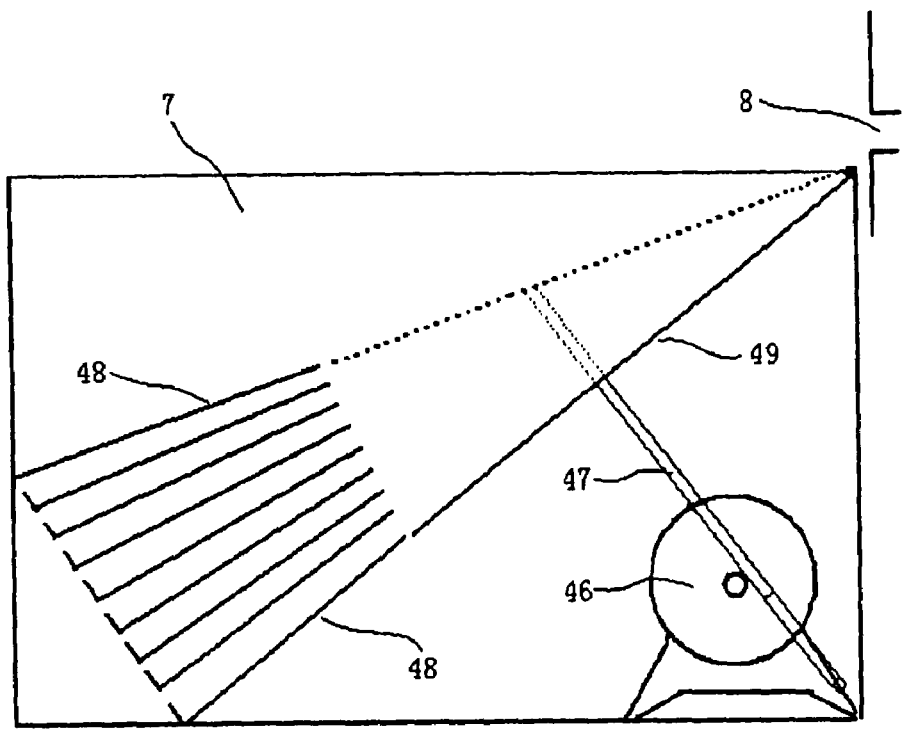
Fig.10

MOBILE ELECTRON BEAM RADIATION STERILIZING APPARATUS

FIELD OF THE INVENTION

The present invention generally relates to an electron beam radiation sterilizing apparatus. In particular, the present invention relates to a mobile electron beam radiation sterilizing apparatus.

BACKGROUND OF THE INVENTION

Since occurrences of "911" event and anthrax event from 2001, anthrax biological attack events via email continuously took place in America and other countries and regions. There has been verified with 17 infection cases, in which many people died. Those infected people have been proven to be infected by contacting mails or packages carrying anthrax bacilli.

Many countries devote much manpower and funds to undertake researches on detection and sterilization of certain bacteria. However, conventional chemical sterilization cannot exterminate anthrax bacilli and take long time with low efficiency, and it cannot meet the needs for detection, quarantine and sterilization of anthrax bacilli for departments with mails of collective disposition and large disposal output. Methods such as microwave, laser or high temperature steam etc. may bring unrecoverable damages to the mails. And plasma electrical discharge method, or low energy electron beam (hundreds of keVs) radiation method can only illuminate anthrax bacilli etc on surfaces of mails or in thin mails, and can not kill anthrax bacilli etc. carried in mails with relative thicknesses. It is a most preferable solution which achieves high speed sterilization for items in mails etc. by high energy electron beam radiation processing.

Sterilization and antisepsis can be achieved by radiation processing with high energy accelerator. The required radiation dose is 25 kGy in a detection standard of medical appliance sterilization. It is pointed out in formal documents of WHO that the kill dosage range for radiation sterilizing spore type bacilli is 10-50 kGy and the kill dosage range for non-spore type bacilli is 0.5-10 kGy. And it is an efficient sterilizing technical solution by using high energy electron beam up to 25 kGy dosage to effectively eliminate different kinds of bacilli including anthrax spore therein.

An electron beam radiating sterilization apparatus generally includes a power supply such as a modulator, an accelerating tube, a beam flow extraction device such as a scanning box, an article transporting system and a control system etc. High energy electron beam radiation sterilization apparatuses have been developed by many organizations with energy range of 2-9 MeV, including "Betaline" developed by IBA corporation, Belgium, "Surebeam" by Titan corporation, USA, "SML5520" by NUCTECH corporation, PRC, etc. These apparatuses have huge volume with heavy weights up to tens of tons, and they need fixed operation sites, some of them even need certain radiation shielding constructions.

The electron beam radiation sterilization safety apparatus are mainly used for preventive sterilization, ensuring no damage to personnel and sites by mails and documents. And existing or potential clients thereof are chief departments at home and aboard. The safety of the chief departments at home have far-reaching political and social influences, since banks (currency sterilization), hospitals (medical wastes and sewage), postage systems hold indispensable functions for daily life and national economy.

In the chief departments of many countries, it is difficult to build huge volume radiation shielding constructions. In addition, many important conferences and activities etc. have no fixed sites, and there are also needs for rapid and complete sterilization by a maneuverable, flexible electron beam radiation sterilization apparatus, which does not require an additional construction, radiating every kind of documents, mails etc. to achieve the safety purpose.

SUMMARY OF THE INVENTION

The present invention is made to solve at least an aspect of the above shortcomings and problems in prior arts.

An object of the invention is to provide a maneuverable and mobile electron beam radiation sterilizing apparatus without needing any additional construction.

Another object of the invention is to provide a compact mobile electron beam radiation sterilizing apparatus, miniaturize designed.

According to an aspect of the invention, a mobile electron beam radiation sterilizing apparatus is provided, comprising: a movable chassis vehicle; a cabinet body installed on the chassis vehicle; an electron accelerator which generates electron beam for articles to be radiation-processed; an accelerator control box, which controls the operation of the accelerator, wherein the electron accelerator is provided in the cabinet body.

According to an embodiment of the invention, the electron accelerator includes an electron beam radiating machine head, which integrally assembles a pulse transformer, a magnetron, a microwave transferring device, an accelerating and scanning integral mechanism, a cooling device, a residual electron beam absorbing device and a radiation shielding system.

According to an embodiment of the invention, the electron accelerator further includes a modulator for modulating voltage of a power supply system into pulse voltage.

According to an embodiment of the invention, the modulator adopts a high frequency charging mode.

According to an embodiment of the invention, the mobile electron beam radiation sterilizing apparatus further includes a ventilating device comprising a ventilating blower, an air inlet passage and an air outlet passage with an inlet of the air inlet passage provided at bottom of the chassis vehicle and an outlet of the air outlet passage provided at top of the chassis vehicle, the inlet and the outlet both provided with moisture proof and dust proof filtering devices.

According to an embodiment of the invention, the mobile electron beam radiation sterilizing apparatus further includes a radiation shielding system which comprises a stationary shielding body covering the accelerator, a pair of rotatable shielding doors rotatably connected to the stationary shielding body and a motor which is driven for switching on or switching off the rotatable shielding doors, so that an enclosed radiating section is formed in the radiation shielding system.

According to an embodiment of the invention, each rotatable shielding door is of a cylinder structure in which a passage for article to be processed entering into the radiating section or retreating therefrom is opened.

According to an embodiment of the invention, the air inlet passage and the air outlet passage are extended through the radiation shielding system in a labyrinth manner and enter into the radiating section.

According to an embodiment of the invention, the labyrinth comprises at least three right-angled corners.

According to an embodiment of the invention, the mobile electron beam radiation sterilizing apparatus further includes an article transporting system having chain wheels, chains to be engaged with the chain wheels and a motor rotating the chain wheels.

According to an embodiment of the invention, an article to be scanned is accommodated in the captive pallet.

According to an embodiment of the invention, hooks are provided on the chains for engaging with the captive pallet so that the captive pallet moves together with the chains.

According to an embodiment of the invention, the article transporting system further includes guide rails for supporting the captive pallet and guiding the movement thereof.

According to an embodiment of the invention, the mobile electron beam radiation sterilizing apparatus further comprises a captive pallet stacking system which comprises: a collecting case; a plurality of fixed guide rails; a movable guide rail; a stepping motor fixed in the collecting case; a dial lever driven by the stepping motor and driving the movable guide rail, wherein an end of the movable guide rail is fixed to an outer side at the outlet for the radiation-processed article, the other end thereof is a free end.

According to an embodiment of the invention, wherein the cabinet body is divided into a radiation cabinet and a control cabinet, the electron accelerator, the article transporting system, the captive pallet stacking system are all provided in the radiation cabinet; a main control system is provided in the control cabinet for controlling the accelerator control box, the captive pallet stacking system, the article transporting system and the radiation shielding system.

According to an embodiment of the invention, a radiation cabinet door is provided between the radiation cabinet and the control cabinet, and a safety interlocking device is provided at the radiation cabinet door.

According to an embodiment of the invention, the safety interlocking device comprises at least one of contact type door interlocking switch, an induction switch and an emergency stop.

According to an embodiment of the invention, the residual electron beam absorbing device is made of material with low atomic number that is electrically and thermally conductible.

According to an embodiment of the invention, the residual electron beam absorbing device forms an electrical circuit with the accelerating and scanning integral mechanism.

According to an embodiment of the invention, the accelerating and scanning integral mechanism is formed of an electron gun, an accelerator tube, a scanning box and an electron beam extraction window integrally and hermetically.

According to an embodiment of the invention, an inner vacuum degree of the accelerating and scanning integral mechanism is up to or above $10^{-5}$.

According to an embodiment of the invention, the control cabinet is further provided with an environmental radiation dose monitoring device.

The advantages and technical effects of the mobile electron beam radiation sterilizing apparatus of the invention are as following:

In the invention, since the electron accelerator and the control system thereof, the ventilating device and the power supply system are all provided in the cabinet body of the chassis vehicle, it has a small volume with flexible maneuverability, which can be transferred rapidly in a short time. In addition, the apparatus has no additional requirement of environment, and does not need any additional construction. The invention can undertake electron beam radiation for kinds of documents and mails and achieve rapid and complete sterilization, reaching safety purpose. Further, there is no damage or residual for the radiation-processed articles. And the apparatus has a high degree of automated assembly with easy operations and safety. Thus, it is suitable for chief departments at home and abroad.

BRIEF DESCRIPTION OF THE DRAWING

These and/or other aspects and advantages of the present invention will be more readily apparent from the following detailed description of preferred embodiments when taken together with the accompanying drawings.

FIG. 8A is a structural schematic view of a rotating shield door 39 in a mobile electron beam radiation sterilizing apparatus according to the invention in an open state;

FIG. 8B is a left side view in FIG. 8A;

FIG. 9A is a structural schematic view of a rotating shield door 39 in a mobile electron beam radiation sterilizing apparatus according to the invention in a closed state;

FIG. 9B is a left side view of FIG. 9A;

FIG. 10 is a structural schematic view of a captive pallet stacking system in a mobile electron beam radiation sterilizing apparatus according to the invention;

Figure 1:
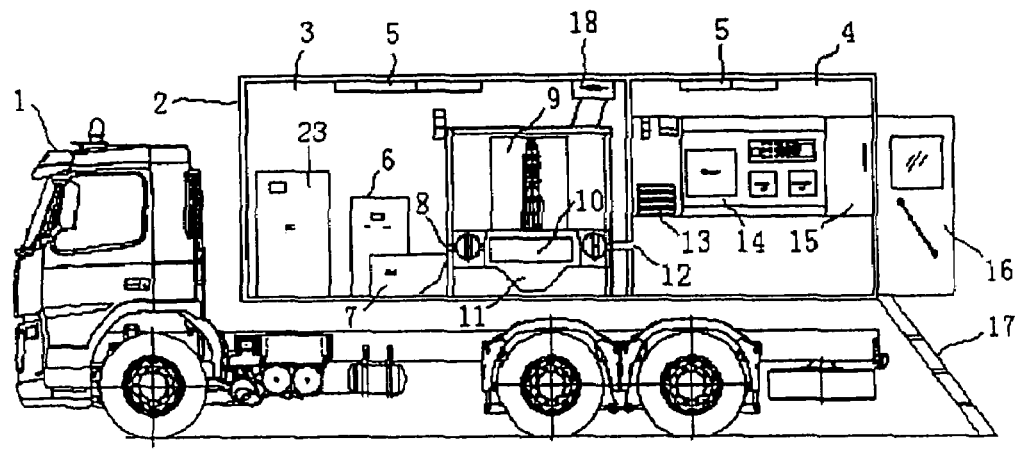
FIG. 1 is a structural schematic view of a mobile electron beam radiation sterilizing apparatus according to the invention.

In the figures, the numerals designate the following components or devices:
1. chassis vehicle;
2. cabinet body;
3. radiation cabinet;
4. control cabinet;
5. illuminating and air conditioning device;
6. electron accelerator;
7. captive pallet stacking system;
8. article outlet;
9. power supply system;
10. article transporting system;
11. radiation shielding system;
12. article inlet;
13. captive pallet;
14. main control system;
15. article cabinet;
16. control cabinet door;
17. ladder;
18. ventilating blower;
19. radiation cabinet door;
20. maintenance door for main control system;
21. maintenance door for radiation machine;
22. electron beam radiation machine;
23. modulator;
24. pulse transformer;

25. magnetron;
26. microwave transmitting device;
27. accelerating and scanning integral mechanism;
28. water cooling device;
29. residual electron beam absorbing device;
30. working chair;
31. control box;
32. monitoring and communicating device;
33. motor;
34. chain wheel;
35. chain;
36. hook;
37. guide rail;
38. stationary shielding body;
39. rotatable shield door;
40. sound and light alerting device;
41. safety interlocking device;
42. environmental radiation dose monitoring device;
43. air inlet passage;
44. air outlet passage;
45. rectangular passage;
46. stepping motor;
47. dial lever;
48. fixed guide rail;
49. movable guide rail;
50. rotating shield door motor;
51. accelerating tube;
53. drift tube;
55. scanning electrical magnet;
56. inboard type ion pump;
57. scanning box;
58. bracket;
61. linear accelerator;
62: electron beam scanning box;
63. radiation-processed object;
64. conveyer;
66. water inlet;
67. water outlet.

DETAILED DESCRIPTION OF THE PREFERRED EMBODIMENTS

Reference will now be made in detail to the embodiment of the present invention, examples of which are illustrated in the accompanying drawings, wherein like reference numerals refer to the like elements throughout. The embodiments are described below to explain the present invention by referring to the figures.

Figure 2:
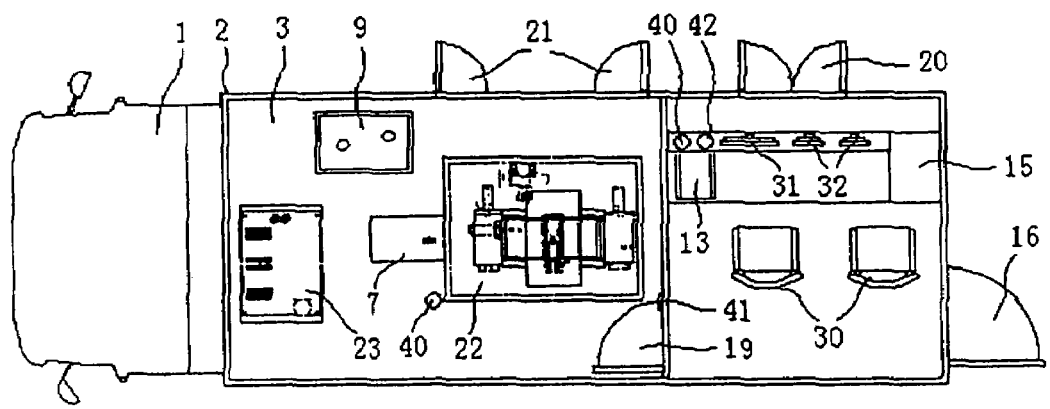
FIG. 2 is a plan view of FIG. 1.

With reference to FIGS. 1 and 2, the mobile electron beam radiation sterilizing apparatus according to the invention comprises a movable chassis vehicle 1, a cabinet body 2 installed on the chassis vehicle 1 in a compact and stable manner, the cabinet body 2 has a radiation cabinet 3 and a control cabinet 4. A control cabinet door 16 is provided at the back of the control cabinet 4 for the passage of personnel. A ladder 17 is provided under the control cabinet door 16 for facilitating the climbing and descending of the personnel. A radiation cabinet door 19 is provided between the radiation cabinet 3 and the control cabinet 4, personnel can enter the radiation cabinet 3 from the control cabinet 4. A control maintenance door 20 for maintaining the main control system is provided at a side of the control cabinet 4. A machine head maintenance door 21 for installation and maintenance of an electron beam radiation machine 22 is provided at a side of the radiation cabinet 3. An illuminating and air conditioning device 5 is further provided in the cabinet body 2.

An electron accelerator 6, a ventilating device 18, an article transporting system 10, a captive pallet stacking system 7, a power supply system 9 and a radiation shielding system 11 are provided in the radiation cabinet 3.

Figure 3:
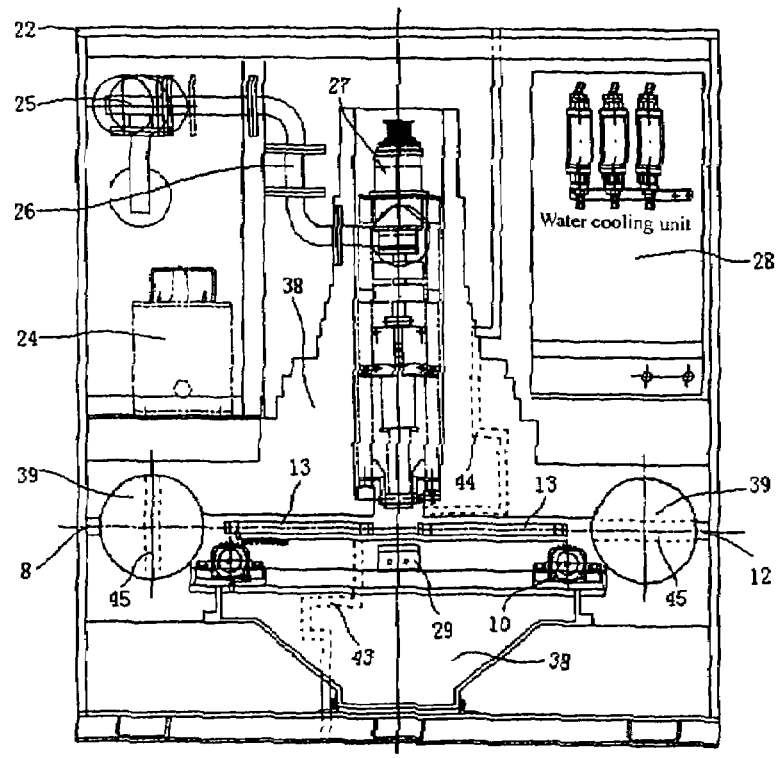
FIG. 3 is a structural schematic view of a radiating machine head in a mobile electron beam radiation sterilizing apparatus according to the invention.

With reference to FIGS. 1, 2 and 3, the electron accelerator 6 is the core device of the invention, which comprises an electron beam radiation machine 22, a modulator 23 and a control box 31. The electron beam radiation machine 22 integrally assembles a pulse transformer 24, a magnetron 25, a microwave transmitting device 26, an accelerating and scanning integral mechanism 27, a water cooling device 28, a residual electron beam absorbing device 29 and the radiation shielding system 11. That is to say, the pulse transformer 24, the magnetron 25, the microwave transmitting device 26, the accelerating and scanning integral mechanism 27, the water cooling device 28, the residual electron beam absorbing device 29 and the radiation shielding system 11 are all installed in the electron beam radiation machine 22. However, the connection relationships among the components are the same with prior art, of which the detailed descriptions are hereby omitted for clarity and brevity purpose. Thus, the volume is reduced in a large scale without influencing technical requirements.

Figure 5:
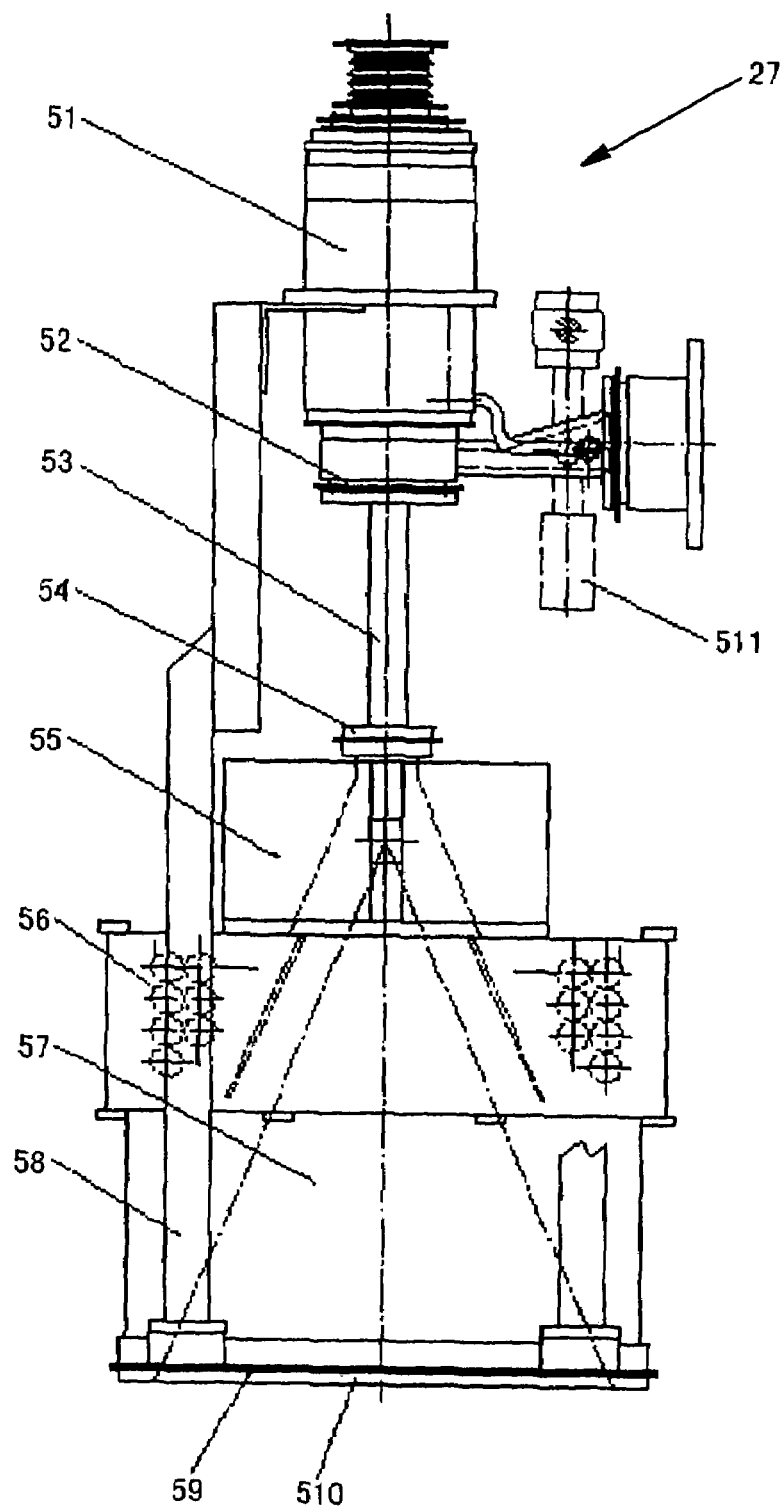
FIG. 5 is a schematic view of an accelerating and scanning integral mechanism 27 that is applicable to the invention.

As an example of the accelerating and scanning integral mechanism 27, FIG. 5 depicts a totally hermetic high degree vacuum electron beam accelerating and scanning integral mechanism. With reference to FIG. 5, the accelerating and scanning integral mechanism 27 comprises an accelerating tube 51, a drift tube 53, a scanning electrical magnet 55 and a scanning box 57 having an inboard type ion pump 56. The accelerating tube 51 can adopt a standing wave accelerating structure with an air discharge port 511, and the standing wave accelerating structure requires high vacuum degree. A scanning electrical magnet 55 is circumferentially provided at the top of the scanning box 57 and connects with the drift tube 53 via a second flange 54. An electron beam extraction window 59 made from material such as titanium foil fixed to the bottom of the scanning box 57 by a third flange 510. A top end of the drift tube 53 is connected with the accelerating tube 51 by a first flange 52. The first flange 52 between the electron accelerating tube 51 and the drift tube 53 is connected via welding by using a flange with thin edge. The second flange 54 between the drift tube 53 and the scanning box 57 is connected via welding by using a flange with thin edge, thus ensuring high air tightness. A vacuum ion pump is provided in the scanning box 57 to form an ion pump 56 with large pumping speed, thus maintaining a high vacuum degree when the accelerating and scanning integral mechanism 27 is working.

Although the embodiment discloses that a drift tube 53 is connected between the accelerating tube 51 and the scanning box 57 by flanges. However, the drift tube 53 is not necessary. For the structure to be more compact and miniaturized, the drift tube 53 is omitted so that the accelerating tube 51 is directly connected with the scanning box 57 in the embodiment of the accelerating and scanning integral mechanism 27.

The accelerating tube 51 and the scanning box 57 are relatively fixed by a bracket 58 to prevent the relative displacement that may damage the welding place of each thin edge flange for being applied with force during installation and use. Meanwhile, the bracket 58 also serves the positioning and fixing member when the accelerating and scanning integral mechanism 27 is provided in the accelerator system.

The first flange 52, the second flange 54 can be welded in many times in a peripheral cutting manner, thus ensuring the crucial members can be used repeatedly. After the integral connection of the accelerating and scanning integral mechanism 27 is completed, it is put into the high temperature exhaust stove for discharging gas by toasting. The gas inside the accelerating and scanning integral mechanism can be discharged through the discharge port 511 of the accelerating tube 51, so that the inner vacuum degree therein can reach up to or above $10^{-5}$ Pa. More preferably, the inner vacuum degree therein can reach up to $10^{-7}$ Pa.

In the structure of the vacuum electron beam accelerating and scanning integral mechanism 27, the accelerating tube and the scanning box having ion pump are positioned and fixed by a bracket, greatly increasing the rigidity of the integral structure. In addition, the second flange and the first flange are welded together by a thin flange, ensuring high air tightness. The accelerating tube adopts a standing wave accelerating structure with a discharge port, which is in favor of miniaturization of the apparatus, so that it can be applied to the mobile electron beam radiation sterilizing apparatus of the invention, achieving the integration and miniaturization of the electron beam radiation machine 22. In addition, it can be put directly into the high temperature discharge stove for integral gas discharging, and the gas is discharged through the discharge port, and the long time accelerating tube vacuum gas discharging process can be avoided, and the inner vacuum degree thereof reaches up to and above $10^{-5}$ Pa, more preferably $10^{-7}$ Pa.

Figure 6:
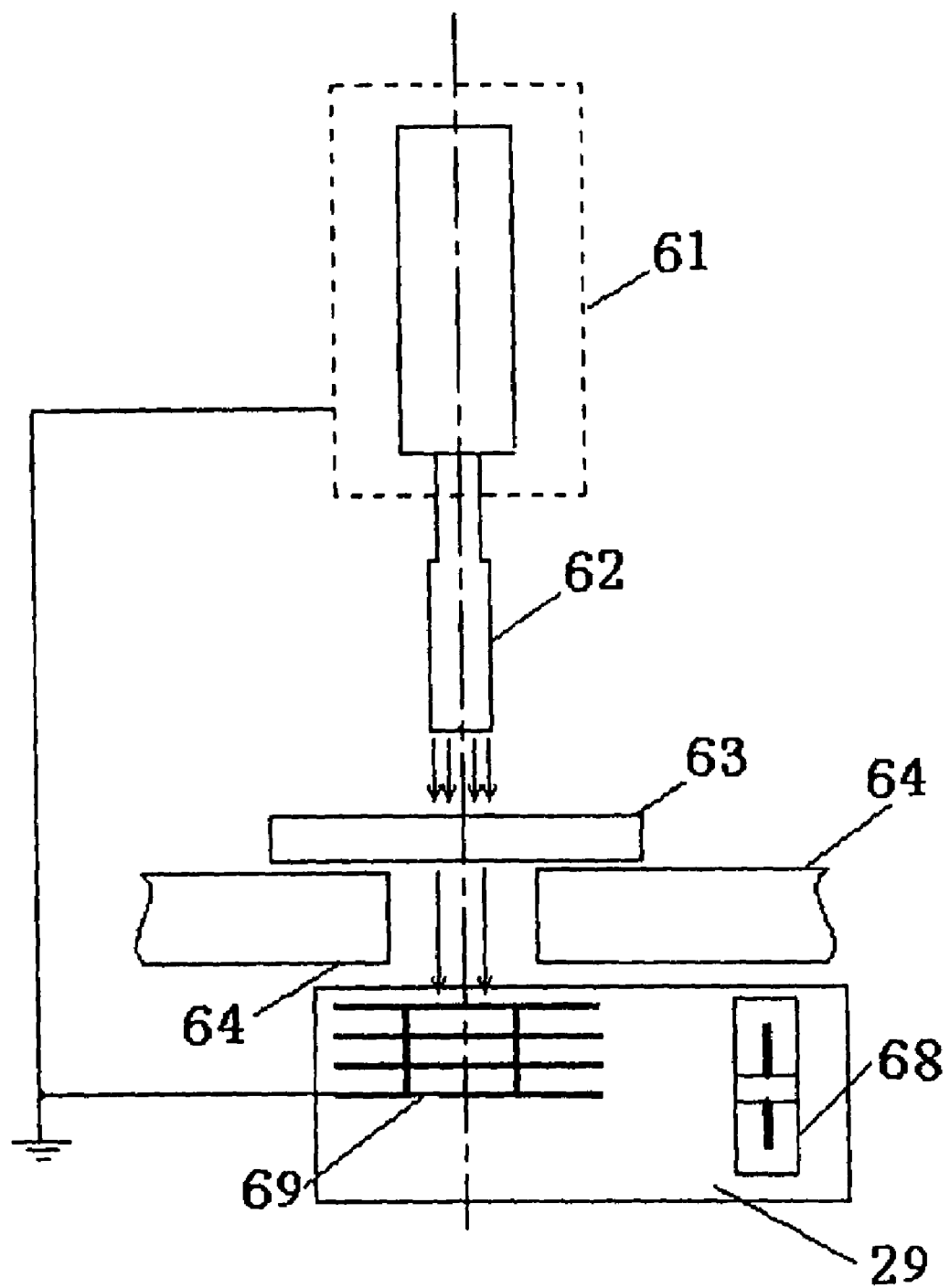
FIG. 6 is a schematic view of a residual electron beam absorbing device 29 that is applicable to the invention.
Figure 7:
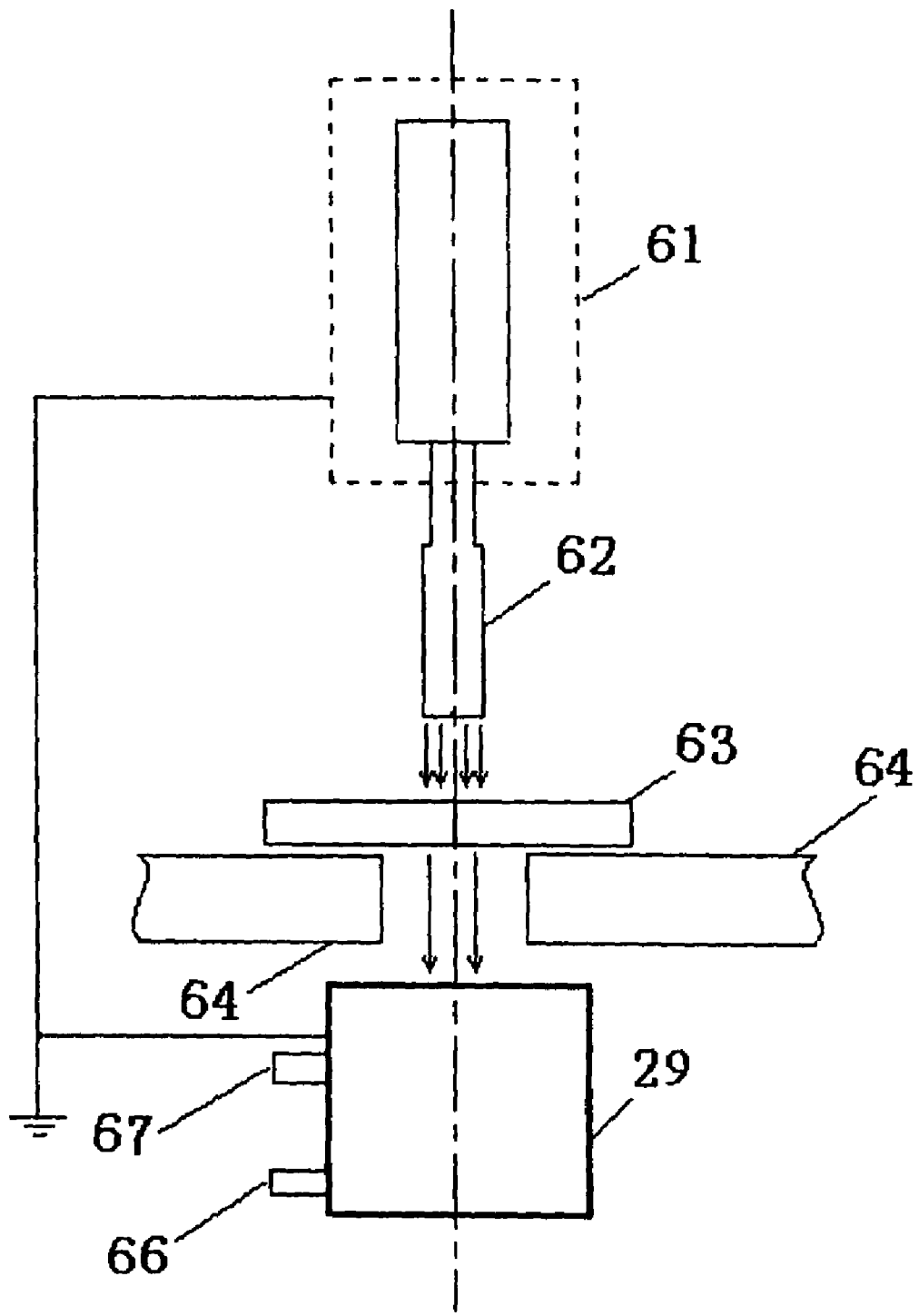
FIG. 7 is a schematic view of another residual electron beam absorbing device 29 that is applicable to the invention.

As an example of the residual electron beam absorbing device, FIGS. 6 and 7 schematically disclose a residual electron beam absorbing device 29.

With reference to FIG. 6, the electron beam radiation device comprises an linear accelerator 61, an electron beam scanning box 62 connected with the linear accelerator 61 and a conveyer 64 provided under the electron beam scanning box 62 on which an radiation processing article 63 can be put. The residual electron beam absorbing device 29 and the linear accelerator 61 are connected by wires to form an electrical circuit. The residual electron beam absorbing device 29 comprises an absorption base 69 having heat radiating tilting pieces made of aluminum material and a blower 68 provided besides the absorption base 69. The wind generated by the blower 68 dissipates heat of the absorption base 69 meanwhile removing the ozone. In the invention, the X ray generating amount can not only be effectively decreased, but also the residual electron beam in the high power accelerator can be prevented from creating high temperature and high voltage section locally. The absorption base 69 of the residual electron beam is cooled by the blower 68 discharging the ozone.

With reference to FIG. 7, the electron beam radiation device comprises an linear accelerator 61, an electron beam scanning box 62 connected with the linear accelerator 61 and a conveyer 64 provided under the electron beam scanning box 62 on which an radiation processing article 63 can be placed. The residual electron beam absorbing device 29 and the linear accelerator 61 are connected by wires to form an electrical circuit. The residual electron beam absorbing device 29 is formed to be a hermetical case structure by aluminum material. A water inlet 66 and a water outlet 67 are provided on the case body, and the residual electron beam absorbing device 29 is cooled by connecting with an outer water cooling system.

In an embodiment of the invention, the assemble structure of the linear accelerator 61 and the electron beam scanning box 62 can be substituted by the above mentioned accelerating and scanning integral mechanism 27. At this time, the residual electron beam absorbing device 29 and the accelerating tube 51 of the accelerating and scanning integral mechanism 27 are connected by wires to form an electrical circuit.

By the residual electron beam absorbing device 29 with the above mentioned structure, the X ray generating amount can not only be effectively decreased, but also the residual electron beam in the high power accelerator can be prevented from creating high temperature and high voltage section locally.

The modulator 23 modulates normal power supply into pulse high voltage. After the pulse high voltage is further raised by a pulse transformer 24, it is supplied to a magnetron 25 in one way and to an electrical gun at the head portion of the accelerating and scanning integral mechanism. The microwave power generated by the magnetron 25 enters into the accelerating and scanning integral mechanism 27 through a microwave transmitting device 26, thus forming an electromagnetic field for accelerating and converging electrons. The emission electrons generated by the electrical gun at the head portion of the accelerating and scanning integral mechanism are accelerated to very high energy in the accelerating and scanning integral mechanism, and are extracted from an electron beam extraction window, such as a titanium window, at the bottom portion of the accelerating and scanning integral mechanism after being scanned into linear distribution by a scanning magnet, becoming high energy electron beam flows for radiating and sterilizing articles to be sterilized.

The modulator 23 adopts a structure of high frequency charging mode, the pulse high voltage has a high stability, and the high voltage amplitude can be easily controlled by the discharge times within a cycle. The high frequency charging mode modulator has a small volume with less weight over conventional linear modulator. However, it is also feasible that the modulator 23 adopts a conventional linear modulator to increase voltage and charge accordingly based on the high voltage transformer.

A water cooling device 28 is installed in the electron beam radiation machine 22 to make the system more compact with smaller volume. The pulse transformer 24, the magnetron 25, the microwave transmitting device 26, the accelerating and scanning integral mechanism 27 and the residual electron beam absorbing device 29 are cooled by the water cooling device 28. In an embodiment of the invention, the water cooling device 28 cools each of the above devices by a plurality of water tubes connected to the pulse transformer 24, the magnetron 25, the microwave transmitting device 26, the accelerating and scanning integral mechanism 27 and the residual electron beam absorbing device 29 in which the cooling water flows. However, the water cooling device 28 can be replaced by other cooling devices, such as a freezing liquid device etc.

Figure 4:
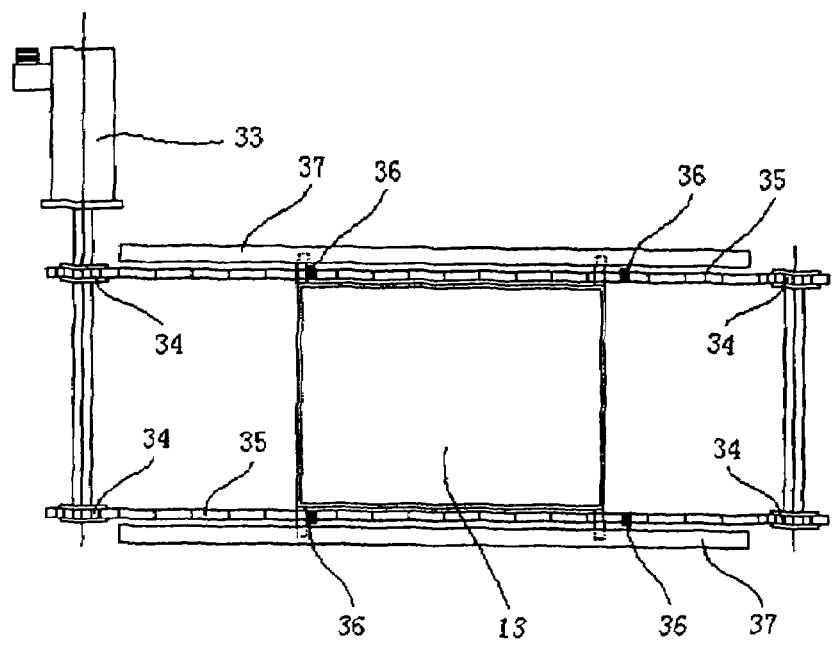
FIG. 4 is a structural schematic view of an article transporting system in a mobile electron beam radiation sterilizing apparatus according to the invention.

With reference to FIG. 4, the article transporting device 10 is composed of a motor 33, chain wheels 34, chains 35, hooks 36 and guide rails 37, in which the guide rails 37 are provided above a position of an outer side the chains 35. The motor 33 rotates the chain wheels 34, which drive the chains 35, the hooks 36 fixed on the chains 35 is pulled or urged so that the captive pallet 13 moves together with the chains 35. The captive pallet 13 is guided and supported by the guide rails 37, thus effectively decreasing the carrying weights of the chains 35, which greatly decreases the danger of being clamped during the movement of the captive pallet 13.

With reference to FIGS. 8A, 8B, 9A and 9B, the radiation shielding system 11 is composed of a fixed shield body 38, a pair of rotatable shielding doors 39 which are rotatably connected to the fixed shield body 38 and a motor 50 rotating the shield doors, so that an enclosed radiation section is formed within the radiation shielding system 11. The radiation shielding system encloses the accelerating and scanning integral mechanism 27, the article transporting system 10 and the residual electron beam absorbing device 29. Each of the rotatable shielding doors 39 is of a cylindrical shape, and can rotate around an axis thereof. A rectangular passage 45 are opened at the middle of the cylinder surface with a dimension mating with that of the captive pallet 13, and the rectangular passage 45 can be connected with the transporting passage of the article transporting system 10. As shown in FIGS. 8A and 8B, when the electron accelerator 6 is not emitting beams, the rotatable shielding doors 39 rotate so that the rectangular passage 45 remains at a horizontal position (please refers to a position of the rotatable shielding door at the right side in FIG. 3), the rotatable shielding doors 39 are opened, and the captive pallet 3 can enter accordingly. On the other hand, as shown in FIGS. 9A and 9B, when the electron accelerator 6 emits beams, the rotatable shielding doors 39 rotate, so that the rectangular passage 45 stops at a vertical position (see a position of the rotatable shielding door at the left side in FIG. 3), the rotatable shielding doors 39 close, so that an enclosed radiating section is formed inside the radiation shielding system, which greatly lowers the leakage rate of the X rays. The ventilating device is used for removing ozone generated during the electron beam radiation. And the ventilating device comprises a ventilating blower 18, an air inlet passage 43 and an air outlet passage 44, in which the inlet of the air inlet passage 43 is provided at the bottom of the chassis vehicle 1, the outlet of the air outlet passage 44 is provided at top of the chassis vehicle 1, moisture proof and dust proof filtering devices are provided at the inlet and the outlet. The air inlet passage 43 and the air outlet passage 44 pass through the radiation shielding system 11 in a labyrinth manner, entering into the radiation section. In an embodiment of the labyrinth form, the air passage includes at least three right-angled corners.

With reference to FIG. 10, a captive pallet stacking system 7 comprises a collecting case, a plurality of fixed guide rails 48, a movable guide rail 49 and a dial lever 47 driven by the stepping motor 46 for driving the movable guide rail 49. The fixed guide rails 48 are arranged in the collecting case in a layered manner according to the dimension of the captive pallet 13. An end of the movable guide rail 49 is fixed outside the outlet 8 of the radiation processed article, the other end thereof forms a free end, so that it can be dialed by the dial lever 47 and butt jointed with the fixed guide rails 48 at different layer. The dial lever 47 is driven by the stepping motor 47, and the rotating angle of the stepping motor is controlled by existing circuits. The captive pallet stacking system 7 collects and stacks the radiation processed article captive pallet 13.

A power supply system 9 comprises a power cable, a power distributing device, a phase sequence protect device, a voltage shortage and overload protect device. The whole device is powered by the power supply system with load balance distribution, phase sequence, voltage shortage and overload protect functions.

The control cabinet is a section for personnel to control the system and rest therein. A main control system 14, working chairs 30, a captive pallet 13 and an article cabinet 15 are provided in the control cabinet.

The captive pallet 13 is made of low Z material, i.e., material with low atomic number, such as aluminum etc. And the wall of the box is very thin. Article to be radiation processed and sterilized is accommodated in the captive pallet 13.

The main control system 14 comprehensively controls the control box 31, the article transporting system 10, the captive pallet stacking system 7, the radiation shielding system 11, the monitor and communication device 32, the sound-light alerting device 40, the safety interlock device 41 and the environmental radiation dose monitoring device 42, so that the operations of each sub-system are in good order and safety. In addition, it further provides a clear and friendly operation interface for users. The control box 31 is provided with a PLC, such as SIMENS S7-200, a touch screen for controlling the electron accelerator 6; safety interlock devices 41, such as a contact type door interlock switch, an induction switch, an emergency stop, provided at the radiation cabinet doors 19 for the interlock protection of the system; a sound-light alerting device 40 for prompting the working state of the electron accelerator 6; and a monitor and communication device 32 for real-time monitoring the radiation cabinet 3 and the outside status of the cabinet body 2 which presents manual notification and alarm before the emission of the electron beams from the electron accelerator 6 to protect the safety of the apparatus and the related personnel.

The environmental radiation dose monitoring device 42 is provided within the control cabinet 4. When the electron accelerator 6 works under an abnormal state or other accidental state so that the environmental radiation dose reaches dangerous level, the environmental radiation dose monitoring device 42 alarms and automatically cuts off the high voltage power supply by the main control system, for protecting personnel from accidental radiation damage. The monitoring and communicating device 32, the sound-light alerting device 40, the safety interlock device 41 and the environmental radiation dose monitoring device 42 adopts existing structures, of which the detailed descriptions are omitted for clarity purpose.

Figure 11:
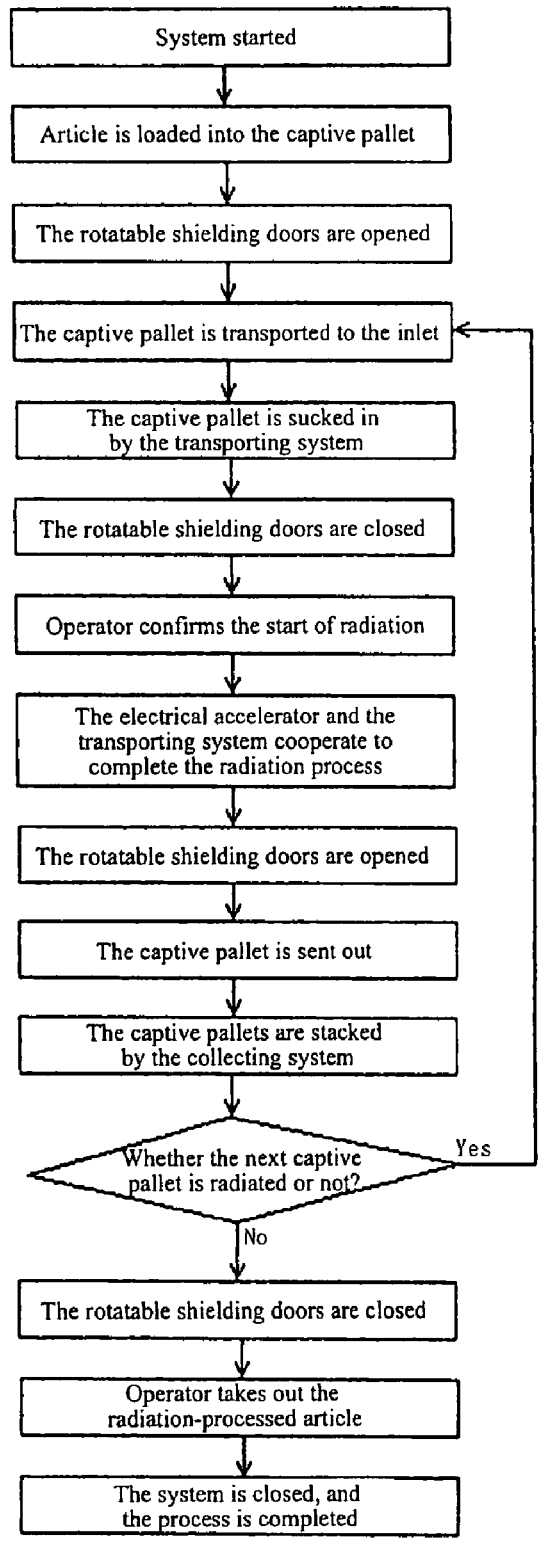
FIG. 11 is a control flow diagram of a main control system in a mobile electron beam radiation sterilizing apparatus according to the invention.

With reference to FIG. 11, a typical system work flow is as following: the electron beam radiation sterilizing system is started; an article to be radiation-processed is put inside the captive pallet 13; a work start button of the main control system is pressed; the rotatable shielding doors of the shielding system are opened by controlling of the main control system; the captive pallet is put to the article inlet 12 by personnel; the captive pallet is sucked into the radiation machine head 22 by the article transporting system 10; the rotatable shielding doors 39 at the inlet are closed; the personnel confirm the starting of radiation; the electron accelerator 6 emits electron beams; the captive pallet 13 passes through the electron beam radiation section at a predetermined speed by the article transporting system 10; the article in the captive pallet is exposed by electron beams, thus completing the sterilization; the electron accelerator 6 stops emitting beams; the rotatable shielding doors 39 at the outlet are opened; the captive pallet 13 is transported out from the radiation-processed article outlet 8 by the article transporting system 10; and the captive pallet after radiation are stacked for collection in sequence by the captive pallet stacking system 7. The next captive pallet is sent in and the radiation is started. After a batch of article radiations are completed, the personnel open the radiation cabinet door and enter into the radiation cabinet, taking out the captive pallet and the articles having been sterilized by radiation.

The mobile electron beam radiation sterilizing apparatus of the invention mainly comprises a chassis vehicle, a cabinet body, an electron beam accelerator and the control system thereof, a transporting system, a radiation shielding system, a main control system, and a power supply system etc. The articles to be radiation-processed are put in the captive pallet, which are transported from the inlet to the lower part of the electron beam accelerator scanning box by the transporting system. With the hermetic space formed by the radiation shielding system, the main control system controls the high energy electron beam flow generated by the electron beam accelerator and the transporting speed of the transporting system. The article to be radiation-processed is uniformly radiated by the electron beams, thus achieving the object of sterilization. Then, the captive pallet is sent out through the outlet by the transporting system into the article collecting case, thus completing the radiation process.

The mobile electron beam radiation sterilizing apparatus of the invention can undertake electron beam radiation for kinds of documents and mails and achieve rapid and complete sterilization, reaching safety purpose. Further, there is no damage or residual radiation for the radiation-processed articles. In addition, the system has a complete hermetic radiation shielding device, thus the ray leakage rate is very low. Moreover, the apparatus has a high degree of automated assembly with easy operations, safety and maneuverability. The apparatus can be rapidly transferred in a short time without any special environmental requirement, which is suitable for chief departments at home and abroad.

The mobile electron beam radiation sterilizing apparatus of the invention can also sterilize the currency of bank, medical devices, or medical disposals. In addition, the invention can also be employed to change color and texture of gems and jades, to sterilize or reduce flavoring, food or cosmetics etc, to promote industrial chemical reaction, and to make intercrosslink of macromolecule materials such as polymer etc.

Although several embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A mobile electron beam radiation sterilizing apparatus, comprising:
    a movable chassis vehicle;
    a cabinet body installed on the chassis vehicle;
    an electron accelerator which generates electron beam for articles to be radiation-processed, wherein the electron accelerator is provided in the cabinet body;
    an accelerator control box, which controls operation of the electron accelerator,
    a radiation shielding system which comprises a stationary shielding body covering the electron accelerator; a pair of rotatable shielding doors rotatably connected to the stationary shielding body, and a motor which is driven for switching on or switching off the rotatable shielding doors, so that an enclosed radiating section is formed in the radiation shielding system,
    wherein each of the rotatable shielding doors is of a cylinder structure through which a passage is formed, wherein the passage is for the articles to be radiation-processed to enter into the radiation section or to retreat therefrom.

2. The mobile electron beam radiation sterilizing apparatus according to claim 1, wherein the electron accelerator includes an electron beam radiating machine head, which integrally assembles a pulse transformer, a magnetron, a microwave transferring device, an accelerating and scanning integral mechanism, a cooling device, a residual electron beam absorbing device and a radiation shielding system.

3. The mobile electron beam radiation sterilizing apparatus according to claim 2, wherein the residual electron beam absorbing device is made of a material with a low atomic number that is electrically and thermally conductible.

4. The mobile electron beam radiation sterilizing apparatus according to claim 2, wherein the residual electron beam absorbing device forms an electrical circuit with the accelerating and scanning integral mechanism.

5. The mobile electron beam radiation sterilizing apparatus according to claim 2, wherein the accelerating and scanning integral mechanism is formed of an electron gun, an accelerator tube, a scanning box and an electron beam extraction window integrally and hermetically.

6. The mobile electron beam radiation sterilizing apparatus according to claim 2, wherein the inner vacuum degree of the accelerating and scanning integral mechanism is up to or above $10^{-5}$ Pa.

7. The mobile electron beam radiation sterilizing apparatus according to claim 1, wherein the electron accelerator further includes a modulator for modulating voltage of a power supply system into pulse voltage.

8. The mobile electron beam radiation sterilizing apparatus according to claim 7, wherein the modulator adopts a high frequency charging mode.

9. The mobile electron beam radiation sterilizing apparatus according to claim 1, further comprising a ventilating device comprising a ventilating blower, an air inlet passage and an air outlet passage with an inlet of the air inlet passage provided at bottom of the chassis vehicle and an outlet of the air outlet passage provided at top of the chassis vehicle, the inlet and the outlet both provided with moisture proof and dust proof filtering devices.

10. The mobile electron beam radiation sterilizing apparatus according to claim 9, wherein the air inlet passage and the air outlet passage are extended through the radiation shielding system in a labyrinth manner and enter into the radiation section.

11. The mobile electron beam radiation sterilizing apparatus according to claim 10, wherein the labyrinth comprises at least three right-angled corners.

12. The mobile electron beam radiation sterilizing apparatus according to claim 1, further comprising an article transporting system having chain wheels, chains to be engaged with the chain wheels and a motor rotating the chain wheels.

13. The mobile electron beam radiation sterilizing apparatus according to claim 12, wherein each of the articles to be radiation-processed is accommodated in a captive pallet which is made of a material with a lower atomic number.

14. The mobile electron beam radiation sterilizing apparatus according to claim 13, wherein hooks are provided on the chains for combining with the captive pallet so that the captive pallet moves together with the chains.

15. The mobile electron beam radiation sterilizing apparatus according to claim 14, wherein the article transporting system further includes a guide rail for supporting the captive pallet and guiding the movement thereof.

16. The mobile electron beam radiation sterilizing apparatus according to claim 12, further comprising a captive pallet stacking system which comprises:
    a collecting case;
    a plurality of fixed guide rails;
    a movable guide rail;
    a stepping motor fixed in the collecting case;
    a dial lever driven by the stepping motor and driving the movable guide rail, wherein an end of the movable guide rail is fixed to an outer side at an outlet for the radiation processed article, the other end thereof is a free end.

17. The mobile electron beam radiation sterilizing apparatus according to claim 16, wherein the cabinet body is divided into a radiation cabinet and a control cabinet,
    the electron accelerator, the article transposing system, the captive pallet stacking system are all provided in the radiation cabinet; a main control system is provided in the control cabinet for controlling the accelerator control box, the captive pallet stacking system, the article transporting system and the radiation shielding system.

18. The mobile electron beam radiation sterilizing apparatus according to claim 17, wherein a radiation cabinet door is provided between the radiation cabinet and the control cabinet, and a safety interlocking device is provided at the radiation cabinet door.

19. The mobile electron beam radiation sterilizing apparatus according to claim 18, wherein the safety interlocking device comprises at least one of contact type door interlocking switch, an induction switch and an emergency stop.

20. The mobile electron beam radiation sterilizing apparatus according to claim 17, wherein the control cabinet is further provided with an environmental radiation dose monitoring device.

* * * * *